United States Patent [19]

Cramer et al.

[11] 4,281,935
[45] Aug. 4, 1981

[54] ADDITIVE INJECTION VALVE

[75] Inventors: Gregory D. Cramer; Irvin B. King; Robert D. Sauerbrunn, all of Seaford; Albert T. Strand, Newark, all of Del.

[73] Assignee: E. I. Du Pont de Nemours and Company, Wilmington, Del.

[21] Appl. No.: 115,214

[22] Filed: Jan. 25, 1980

[51] Int. Cl.³ ............................................. F16K 1/02
[52] U.S. Cl. ............................... 366/174; 137/243.7; 137/340; 137/605; 137/897; 141/105; 251/145; 366/338
[58] Field of Search ............... 137/243.3, 243.6, 243.7, 137/561 R, 605, 606, 897; 251/145; 366/173, 338, 339; 141/9, 105, 107, 367, 386; 73/422 R, 422 GC

[56] References Cited

U.S. PATENT DOCUMENTS

| | | | |
|---|---|---|---|
| 582,507 | 5/1897 | Marchaut | 251/145 X |
| 1,489,990 | 4/1924 | Donohoe | 137/243.7 |
| 2,177,265 | 10/1939 | Rath | 137/243.6 |
| 3,371,680 | 3/1968 | Alcorn | 137/340 |
| 3,470,912 | 10/1969 | Bydal | 366/338 X |
| 3,664,638 | 5/1972 | Grout | 366/338 |
| 3,716,346 | 2/1973 | Greene | 137/605 X |
| 4,026,324 | 5/1977 | King | 137/605 |
| 4,195,654 | 4/1980 | Coley | 137/605 X |

FOREIGN PATENT DOCUMENTS

1205675  9/1970  United Kingdom ..................... 366/174

*Primary Examiner*—Robert G. Nilson

[57] ABSTRACT

A valve for adding ingredients to or sampling the fluid flowing through the valve includes an adjustable solid stem which can be extended through the flow path of a pipeline to form a seal with a seat positioned directly opposite the stem. An injection nozzle is fitted into the seat to permit addition of ingredients or sampling of the fluid when the stem is retracted from the seat. When the stem is seated, flow still occurs in the flow path.

6 Claims, 4 Drawing Figures

ADDITIVE INJECTION VALVE

BACKGROUND OF THE INVENTION

This invention relates to a valve and more particularly to a valve for injecting or ejecting fluid to or from a fluid stream flowing through a path in the valve body.

King and Kendall in U.S. Pat. No. 4,026,324 disclose a valve which may be used for injecting fluid additives into a flowing stream in a manufacturing process in which the valve closure means is located in the flowing process stream. The valve may be partially disassembled for cleaning without shutting down the manufacturing process in which the valve operates. This valve utilizes a grooved stem 40 to supply additives to the process flow stream with the grooves being enclosed by a stem cylinder 30 into which stem 40 is fitted. Disassembly problems may be created if a cementitious additive is injected which, if the time and temperature conditions were right after the valve was closed off, could cement parts 30 and 40 together.

SUMMARY OF THE INVENTION

The instant invention overcomes these problems by providing a valve having a body member with a flow path therethrough from an inlet end to an outlet end. The valve has a stem connected to the body member which is movable through the flow path to engage a valve seat located directly opposite the valve stem in the body member. The valve seat has an upper surface exposed to the flow path through the valve body member and a passage therethrough extending from the upper surface. A removable nozzle is fitted in the valve seat passage and extends from the upper surface of the valve seat to a location outside the valve body member.

The valve stem may be made in two pieces with a means for coupling the two pieces together for independent rotation and constrained advancement of the stem pieces whereby the stem may be advanced to the valve seat and then the valve stem may be rotated relative to the valve seat to permit cleaning the seating surfaces.

DETAILED DESCRIPTION OF THE ILLUSTRATED EMBODIMENTS

Figure 1:
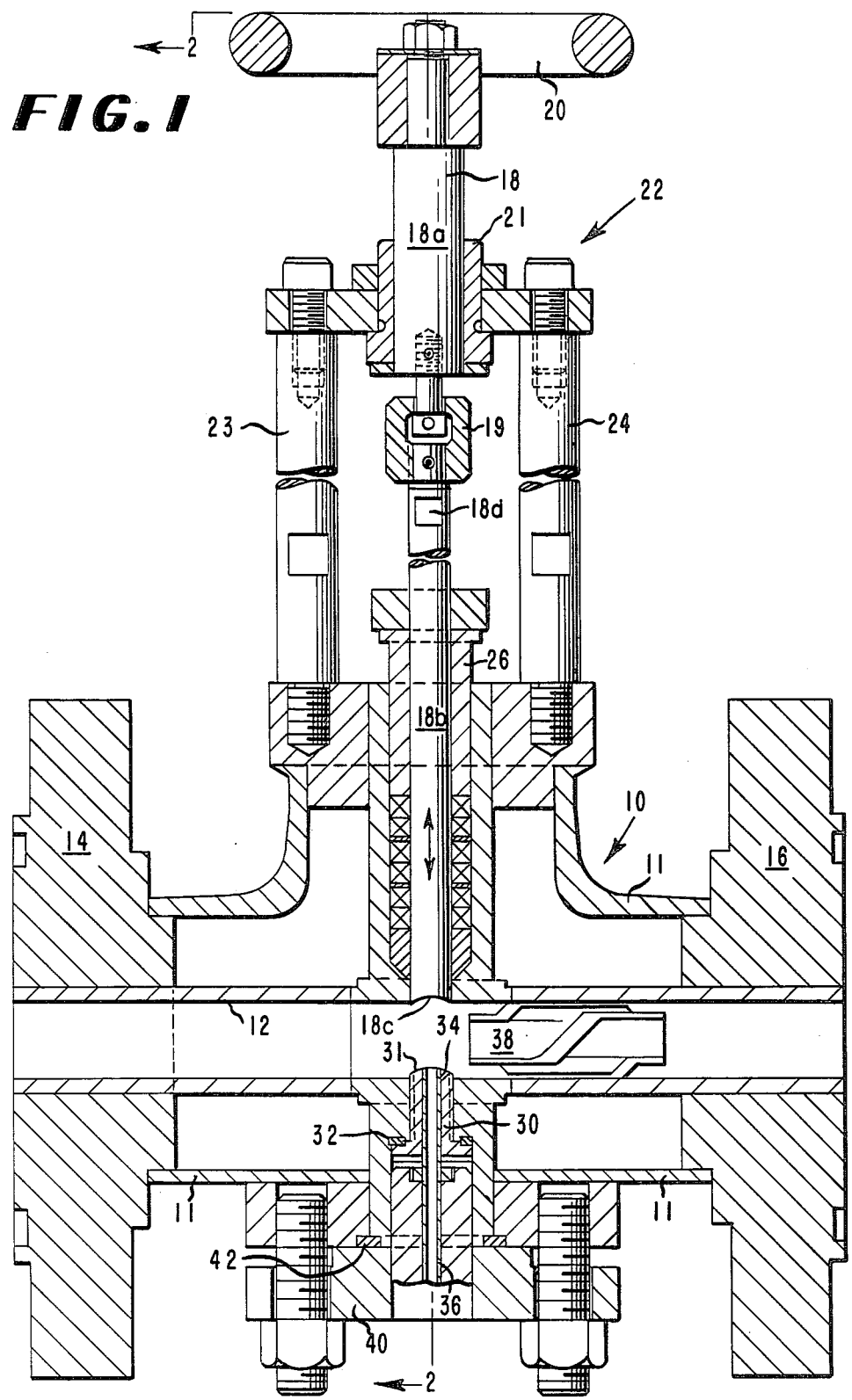
FIG. 1 is a cross-sectional side elevation view of the valve of this invention.
Figure 2:
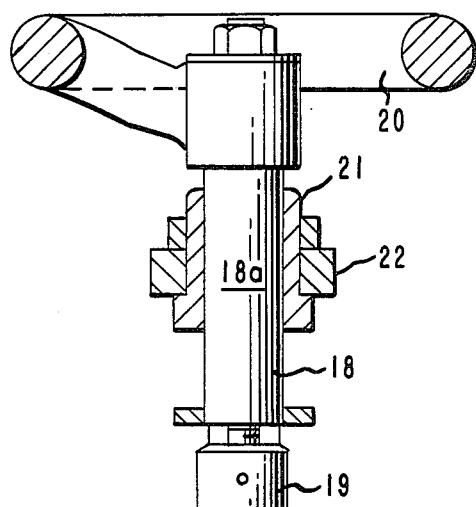
FIG. 2 is a cross-sectioned end elevation view of the valve of FIG. 1.

Referring to FIGS. 1 and 2 the valve body 10 has a fluid flow path 12 therethrough from an inlet end flange 14 to an outlet end flange 16 for connection to subsequent piping. A valve control mechanism is seen to comprise a valve stem 18 which may be actuated by a handwheel 20 connected to one end of the valve stem. The valve stem extends from the handwheel through a yoke 22 supported by studs 23, 24 threaded into valve body 10. The yoke includes a threaded bushing 21 through which stem 18 advances as it is rotated. At its other end the valve stem 18 extends through packing gland 26 to the flow path 12 in valve body 10. The stem is essentially a two piece affair 18a, 18b joined by coupling 19 which clasps stem pieces 18a and 18b such that they may rotate independently but are constrained to advance together. If desired for cleaning purposes the seating surface 18c of stem 18 may be rotated respective to and in contact with the surface 31 of seat 30. This may be accomplished by turning stem piece 18b with a wrench engaging the flats 18d on the stem piece. The valve body 10 is provided with jacket means 11 for circulation of heat transfer fluid, as for maintaining molten polymer at the required temperature.

The valve body member 10 is provided with a seat 30 located directly opposite the valve stem 18. The seat has an upper surface 31 protruding into the flow path and is threaded into the valve body against a gasket 32 to prevent leakage. There is a passage 34 through the seat which contains a closely fitting removable nozzle 36 which is in the form of tubing extending from upper surface 31 of the seat to a location outside the valve body where it may be connected to a source of a pressurized additive for injection into the flow path 12. There is a flow inverter 38 similar to that disclosed in U.S. Pat. No. 3,470,912 located downstream of the valve seat 30 for inverting the injected additive from the wall to the center of the flow stream for faster dispersion. The removable nozzle 36 is an integral part of the flanged plug 40 which is bolted onto the valve body member 10 and sealed against the body member via gasket 42.

Figure 3:
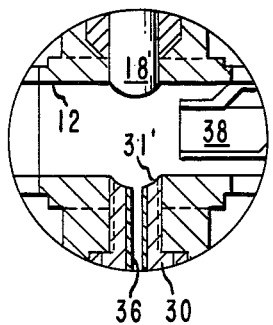
FIGS. 3 and 4 are cross-sectioned views of alternate complementary seat and stem arrangements for the valve of this invention.
Figure 4:
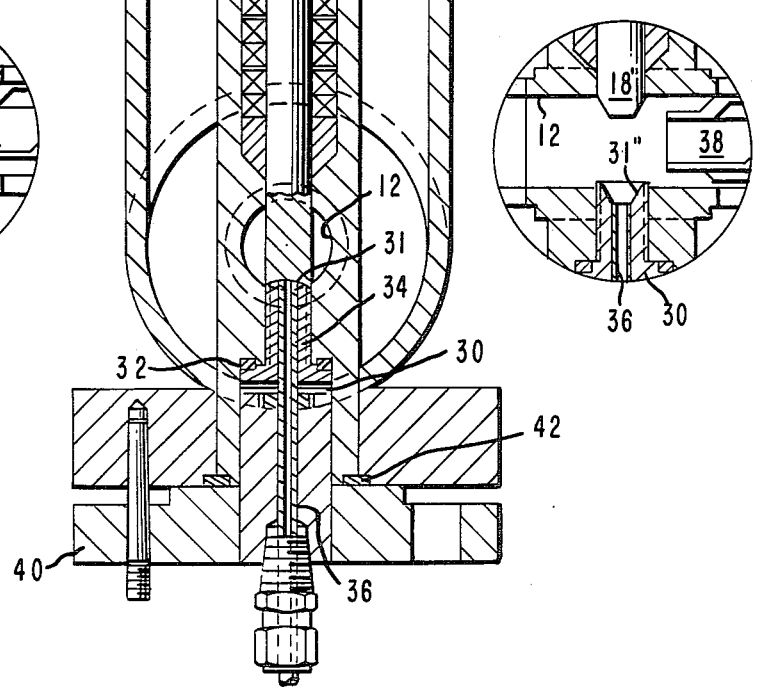

Alternate embodiments of the valve seat and stem seat arrangements showing complementary contours involving recessed seat surfaces 31' and 31" along with respective protruding valve stem seats are evident from FIGS. 3 and 4.

The valve may be used to inject additives into the process flow path by injecting additives through nozzle 36 in seat 30. In operation the nozzle 36 is exposed to the flow path 12 by turning handwheel 20 in one direction causing stem 18 to be withdrawn from seat 30. Turning the handwheel in the opposite direction results in reversed motion of the stem and the seating surfaces of stem 18 and the seat 30 are brought together thereby closing off the nozzle 36.

In a similar fashion the valve may be used to remove sample material from the flow path 12 by applying a lesser pressure at nozzle 36.

The novel construction of the valve of the present invention facilitates removal of the nozzle 36 without process shutdown. The seating surfaces are closed to isolate nozzle 36 from the flow path 12 and then the whole nozzle assembly may be easily unbolted and removed. The nozzle may be then cleaned or repaired or simply replaced with a nozzle having different dimensions such as a larger or smaller I.D.

We claim:

1. A valve for adding ingredients to or sampling the fluid flowing through the valve comprising: a body member having a fluid flow path therethrough from an inlet end to an outlet end; a valve stem connected to the body and movable through said flow path to engage a valve seat located directly opposite said valve stem in said body member, said valve seat having an upper surface exposed to said flow path, said seat having a passage therethrough extending from said upper surface; and removable tubing closely fitting in said passage extending from said upper surface to a location outside said body member.

2. The valve as defined in claim 1, said upper surface of said seat and the portion of the valve stem which engages said upper surface being complimentary contoured.

3. The valve as defined in claim 1, including a flow inverter located in said flow path downstream of said valve seat.

4. The valve as defined in claim 1, said stem being at a location intermediate said inlet and said outlet ends.

5. The valve as defined in claim 1, said upper surface protruding into said flow path.

6. A valve for adding ingredients to or sampling the fluid flowing through the valve comprising: a body member having a fluid flow path therethrough from an inlet to an outlet; a two-pieced valve stem connected to the body and movable through said flow path to engage a valve seat located directly opposite said valve stem in said body member, said valve seat having an upper surface protruding into said flow path, said seat having a passage therethrough extending from said upper surface; removable tubing closely fitting in said passage extending from said upper surface to a location outside said body member; and means coupling the two pieces of said valve stem together for permitting independent rotation and constrained advancement of said pieces whereby the stem may be advanced to said valve seat surface and then the valve stem may be rotated relative to the valve seat.

* * * * *